United States Patent
Zhao et al.

(10) Patent No.: US 11,579,432 B2
(45) Date of Patent: Feb. 14, 2023

(54) OPTICAL SYSTEM FOR A SIDE-VIEWING ENDOSCOPE, AND SIDE-VIEWING ENDOSCOPE

(71) Applicant: OLYMPUS WINTER & IBE GMBH, Hamburg (DE)

(72) Inventors: Jianxin Zhao, Hamburg (DE); Alrun Thuemen, Hamburg (DE)

(73) Assignee: OLYMPUS WINTER & IBE GMBH, Hamburg (DE)

(*) Notice: Subject to any disclaimer, the term of this patent is extended or adjusted under 35 U.S.C. 154(b) by 673 days.

(21) Appl. No.: 16/434,868

(22) Filed: Jun. 7, 2019

(65) Prior Publication Data
US 2019/0285869 A1      Sep. 19, 2019

Related U.S. Application Data

(63) Continuation of application No. PCT/EP2017/081455, filed on Dec. 5, 2017.

(30) Foreign Application Priority Data

Dec. 15, 2016   (DE) .................... 10 2016 225 097.3

(51) Int. Cl.
*G02B 23/24*      (2006.01)
*A61B 1/00*       (2006.01)
(Continued)

(52) U.S. Cl.
CPC ...... *G02B 23/2423* (2013.01); *A61B 1/00174* (2013.01); *G02B 17/045* (2013.01); *G02B 27/0018* (2013.01); *A61B 1/04* (2013.01)

(58) Field of Classification Search
CPC .. G02B 23/243; G02B 23/2423; G02B 13/00; G02B 23/02; G02B 5/04; A61B 1/00096; A61B 1/00179

See application file for complete search history.

(56) References Cited

U.S. PATENT DOCUMENTS

| 4,138,192 A | 2/1979 | Yamasita |
| 4,655,557 A | 4/1987 | Takahashi |

(Continued)

FOREIGN PATENT DOCUMENTS

| DE | 24 58 306 A1 | 6/1975 |
| DE | 10 2016 214 025 A1 | 2/2018 |

(Continued)

OTHER PUBLICATIONS

International Search Report dated Mar. 1, 2018 received in PCT/EP2017/081455.

*Primary Examiner* — Alexandra L Newton (74) *Attorney, Agent, or Firm* — Scully, Scott, Murphy & Presser, P.C.

(57) ABSTRACT

An optical system having a viewing angle θ relative to a longitudinal axis including: a prism group to deflect incident light by reflection at first and second surfaces including prisms with mutually adjacent boundary surfaces arranged in pairs and separated by a gap, a total reflection of incident light from outside a field of view takes place at a boundary surface between a prism and a corresponding gap, the prism group has a cylindrical envelope (D), and an input-side prism is configured to have a wedge-shape with angle β and an optical path length α; an entry surface of the prism has a length L, which is a length of a line of intersection of the entry surface with a plane that is spanned by a central beam path; and the first prism meets the conditions: α<cos θ·tan β·D/2 and L<D/cos θ.

10 Claims, 5 Drawing Sheets

(51) Int. Cl.
*G02B 17/04* (2006.01)
*G02B 27/00* (2006.01)
*A61B 1/04* (2006.01)

(56) References Cited

U.S. PATENT DOCUMENTS

| | | | |
|---|---|---|---|
| 5,632,718 A | 5/1997 | Igarashi et al. | |
| 7,280,283 B1* | 10/2007 | Kasai | G02B 9/60 |
| | | | 359/656 |
| 2018/0028050 A1 | 2/2018 | Zhao et al. | |
| 2018/0055341 A1* | 3/2018 | Tuscher | A61B 1/055 |

FOREIGN PATENT DOCUMENTS

| | | |
|---|---|---|
| JP | 50-91333 A | 7/1975 |
| JP | 60-140313 A | 7/1985 |
| JP | 2006-039259 A | 2/2006 |
| WO | 01/01186 A1 | 4/2001 |

\* cited by examiner

OPTICAL SYSTEM FOR A SIDE-VIEWING ENDOSCOPE, AND SIDE-VIEWING ENDOSCOPE

CROSS-REFERENCE TO RELATED APPLICATION

The present application is a continuation of PCT/EP2017/081455 filed on Dec. 5, 2017, which is based upon and claims the benefit to DE 10 2016 225 097.3 filed on Dec. 15, 2016, the entire contents of each of which are incorporated herein by reference.

BACKGROUND

Field

The present disclosure relates to an optical system for a side-viewing endoscope with a central beam path that has a distal lateral viewing angle θ relative to a longitudinal axis of an endoscope shaft of the endoscope, as well as a corresponding side-viewing endoscope.

Prior Art

The optical elements of an optical system, generally one or more lenses, map incident light bundles from a field of view onto a light-sensitive surface of an image sensor. These light bundles run within a beam path defined by the optical assemblies of the optical system, more precisely by their optical elements.

The field of view of the optical system refers to an area or an interval of viewing angles within which events or changes in the object space can be perceived with the optical system. Incident light bundles from the field of view are mapped on the light-sensitive surface of the image sensor. With a rectangular image sensor, the field of view is defined by a horizontal viewing angle and by a vertical viewing angle. The horizontal and vertical viewing angles are limited by the edges of the imaging format, which in turn depends on the size and shape of the image sensor. With a rectangular image sensor, the vertical viewing angle is typically smaller than the horizontal viewing angle (landscape format). The horizontal viewing angle and the vertical viewing angle are thus the maximum possible angles of incidence below which beams of light can enter the optical system and still be mapped on the light-sensitive surface of the image sensor.

If light bundles enter the optical system with larger angles, reflections occur at the optical elements. These light bundles also cause diffuse scattering or reflection on a tube or lens tube in which the optical elements of the optical system are received. These reflections, also often referred to as "flare" or "lens flare", adversely affect the image quality of the optical system.

Traditionally, the entry of such light bundles is reduced by mechanical masks or apertures within the optical system. However, masks or apertures often lead to strong vignetting, i.e. shading up to the edge of the image. Such masks also require very tight manufacturing tolerances for the optical system.

Figure 1:
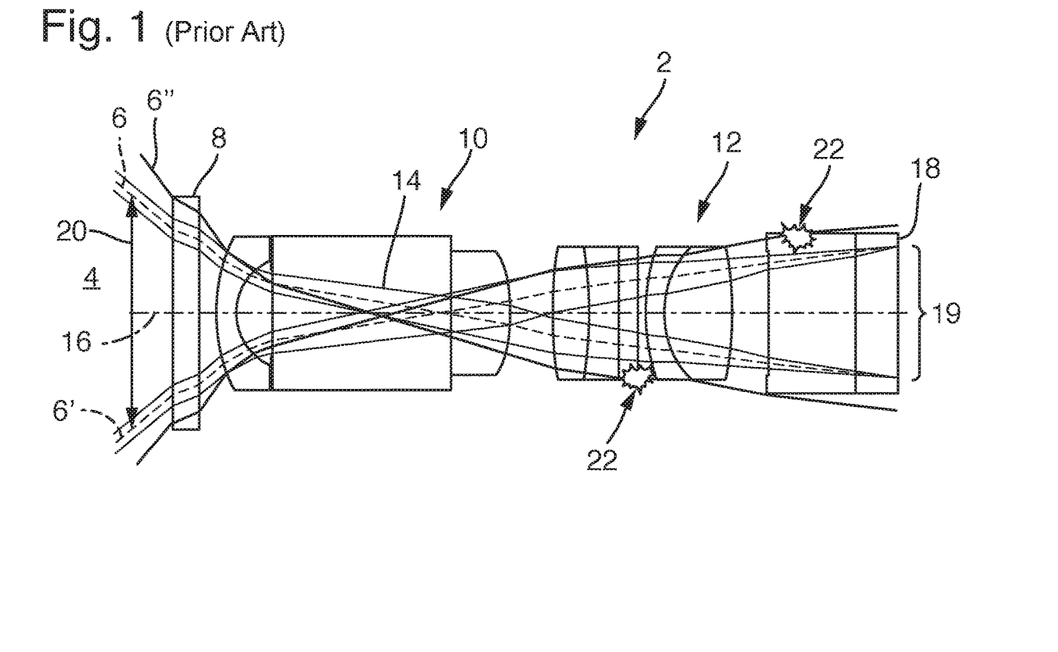
FIG. 1 illustrates an optical system according to the prior art, in a schematically simplified longitudinal section.

FIG. 1 shows an optical system 2 according to the prior art in a schematically simplified longitudinal section view. Incident light bundles 6 (of which only one bears a reference number for reasons of clarity) from an object space 4 first fall upon an entry window 8. The optical system 2 is, for example, a component of a surgical instrument, furthermore the optical system 2 of an endoscope, for example. Within an endoscope, the entry window 8 hermetically seals the interior space of an endoscope shaft at its distal end with respect to an exterior space or object space 4. If the light bundles 6 have passed through the entry window 8, they encounter a distal optical assembly 10 and afterward reach a proximal optical assembly 12. The distal and proximal optical assemblies 10, 12 define a beam path 14 in the optical system 2.

A field of view 20 is situated in the object space 4, which is defined by a horizontal and a vertical viewing angle. The longitudinal section shown in FIG. 1 shows a section along a vertical plane, for example. Consequently, the vertical viewing angle can be seen. It is the angle between an optical axis 16 of the optical system 2 and the light bundle 6 which just strikes a light-sensitive surface 19 of an image sensor 18. The field of view 20 is indicated schematically in FIG. 1 with an arrow. The distal optical assembly 10 and the proximal optical assembly 12 map incident light bundles 6, 6' from the field of view 20 on the light-sensitive surface 19 of the image sensor 18.

If, however, light bundles 6" from outside of the field of view 20 enter the optical system 2, these cause diffuse scattering and reflections within the optical system 2. For example, diffuse scattering occurs on an interior wall of a tube or of a lens tube of the optical system 2. This is indicated in FIG. 1 with star shaped markings which are intended to indicate scattering centers 22. These reflections or scatterings cause "flare" or "lens flare", a phenomenon which adversely affects the image quality of the optical system 2.

Figure 4A:
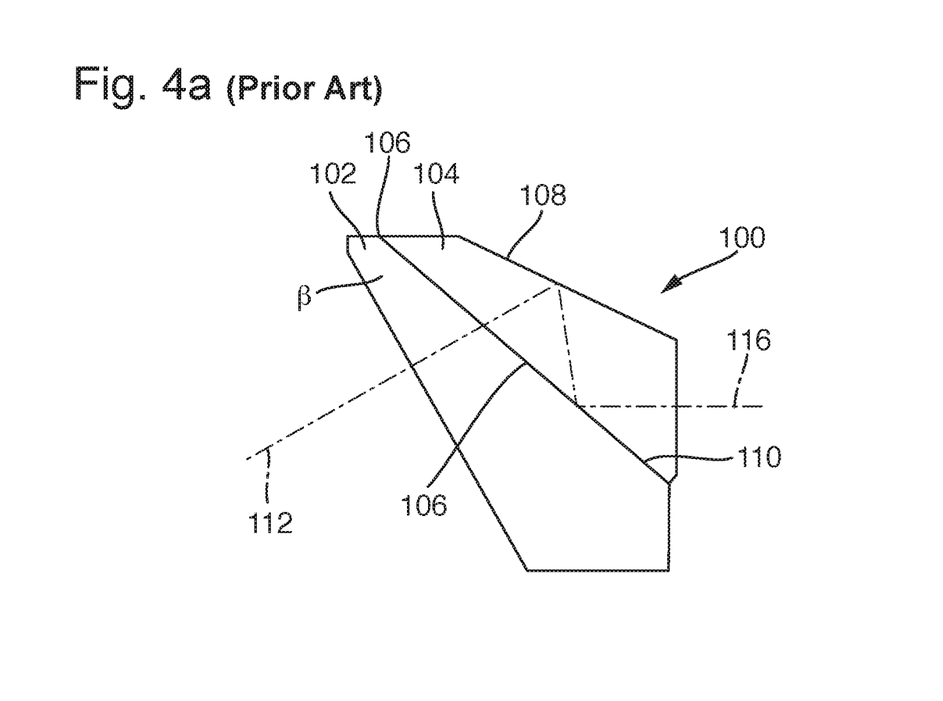
FIGS. 4a and 4b illustrate a prism group with two prisms according to the prior art, as well as details of the first prism of the prism group.
Figure 4B:
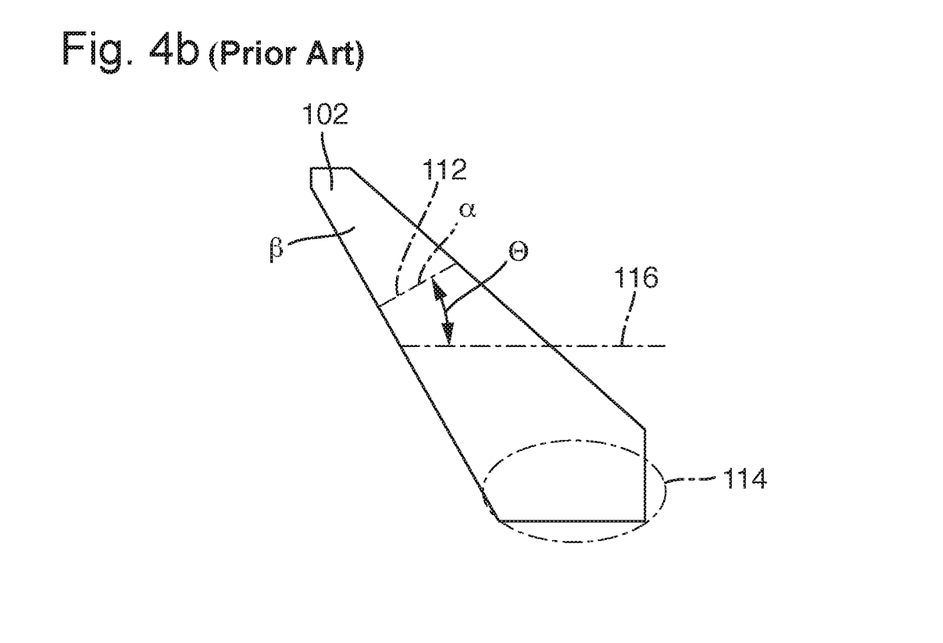

FIG. 4 schematically depicts a distal optical assembly 100 with a prism group having two prisms which are known from the prior art. The group consisting of a first prism 102 and a second prism 104 is depicted in a cross-section in FIG. 4a) together with the central beam path 112. Between the two prisms 102 and 104, there is a gap 106 which is filled with air or another medium.

The central beam path 112 begins in the field of view on the left side of the image and first runs at an angle to the central axis of the endoscope which runs horizontally in the present view. The beam path 112 enters the first prism 102 through a first boundary surface, enters the second prism 104 through the gap 106, and is reflected at the mirrored rear boundary surface of the second prism 104. The beam path 112 runs within the second prism back to the gap 106 where a reflection takes place, for example a total reflection, at the second reflective surface 110 which deflects the central beam path 112 so that it for example coincides with the central longitudinal axis 116 of the endoscope.

FIG. 4b shows the first prism 102 of the prism group from FIG. 4a in greater detail. The prism is cut on the top side, is designed in the shape of a wedge, and has a wedge angle β. The part of the central beam path 112 that runs through the first prism 102 has a length α and an angle θ to the central longitudinal axis 116 of the endoscope which accordingly defines the lateral viewing angle of the endoscope. As discernible in FIG. 4a as well as in FIG. 4b, primarily the top part of the prism group is used for the optical beam path around the central beam path 112 whereas the bottom part is not used optically. The optically unused glass volume is identified by reference number 114 and represents a more-or-less dead volume or ballast.

SUMMARY

An optical system that achieves this object for an endoscope with a direct view is disclosed in the unpublished German patent application DE 10 2016 214 025.6, the disclosed content of which is fully incorporated herein by reference It is an object to provide an improved optical system and an improved surgical instrument with a lateral viewing direction with such an optical system, wherein the optical system is to be less sensitive to incident light bundles outside a field of view.

Such object can be achieved by an optical system for a side-viewing endoscope with a central beam path that has a distal lateral viewing angle θ relative to a longitudinal axis of an endoscope shaft of the endoscope comprising a distal optical assembly having a prism group which is designed to deflect incident light from a field of view defined around the lateral viewing angle in a direction of the longitudinal axis of the endoscope shaft by means of reflection at a first reflective surface and at a second reflective surface, and comprises two or more prisms, the mutually adjacent boundary surfaces of which are arranged in pairs parallel to each other and are separated by a gap in each case, wherein total reflection of some of the incident light from outside a field of view takes place at a boundary surface between a prism and the subsequent gap, wherein the prism group has a cylindrical envelope with a diameter D, and an input-side first prism of the prism group is configured having a wedge-shape with a wedge angle β and an optical path length α of the central beam path, wherein an entry surface of the first prism has a length L that is defined as a length of a line of intersection of the entry surface with the plane that is spanned by the central beam path, and the first prism meets the conditions:

$$\alpha < \cos\theta \cdot \tan\beta \cdot D/2 \text{ and } L < D/\cos\theta.$$

The prism group accordingly provides an angle-dependent optical filter with which incident beams of light entering the optical system from outside the field of view are reflected out of the beam path. Despite the lateral view, no vignetting occurs, and there are also no particularly strict requirements for centering or adjustment of the prism group in the optical system. Furthermore, such a prism group is inexpensive to manufacture and can be readily integrated in the optical system.

The prism group can be rotatably incorporated in the optical system. For example, the prism group in the optical system can be rotatable on one axis which at least approximately corresponds to the optical axis of the optical system, such as an optical axis of the distal optical assembly of the optical system. It is possible by rotating the prism group to limit the field of view in a variable manner on different sides with the aid of the prism group.

The two conditions that the first prism meets ensures that the angle-dependent optical filtering is combined, by means of total reflection, with a compact design which fits in a cylindrical envelope and takes into account the lateral viewing angle θ. The conditions ensure that the first wedge, or the first prism, is cut very thinly. At the same time, its left and right sides are cylindrical and identical with the corresponding sides of the second and possibly third prism. This enables the prisms to be easily glued together. The optical path length in the first prism is kept short, which in particular simplifies the prism design for prisms with a larger diameter.

The prism group can have three prisms, wherein the second prism is designed wedge-shaped, such as with a wedge angle of 2·β, wherein the wedge angle of the second prism borders a side of the first prism opposite the wedge angle of the first prism, and the wedge angle of the first prism borders a side of the second prism opposite the wedge angle of the second prism so that the gaps between the three prisms are angled relative to the central beam path in different directions. The second gap is accordingly rotated relative to the first gap by an amount that ensures that light beams from outside of the viewing range are removed out of the beam path in a completely symmetrically reflected manner in order to symmetrically remove ghost images and flares. For this reason, the wedge angle of the middle prism is twice as large as the wedge angle of the first prism. This selection achieves symmetry of the two gaps relative to the central beam path of the prism group.

The gap or gaps can be filled with a medium that has a lesser optical density than a glass used for the prisms, wherein the medium can be a vacuum, an inert atmosphere or air. This selection ensures that a total reflection becomes possible which occurs in the transition from an optically denser medium to an optically thinner medium, but not in the transition from an optically thinner to an optically denser medium.

The first prism and/or the second prism can have a lower cut and/or an upper cut. By means of this measure, it becomes possible to use the upper and/or lower cuts of the prisms as a stop during assembly. The corresponding cuts form deviations from the cylindrical envelope, such as chords within the circular cross-section formed by the cylindrical envelope. Accordingly, spaces in a holder can be spared so that more elements such as heating elements can be installed in the system. The lower or upper cuts of the prisms in the prism group can be formed stacked in height. This facilitates the use of the cuts as stops for assembly.

A proximal optical assembly and at least one image sensor or an eyepiece proximal to the proximal optical assembly can also be provided. A lens group can be used as the proximal optical assembly that focuses the light from the distal optical assembly on a following image sensor or, in the case of stereoendoscopy, on a pair of following image sensors. The proximal assembly can also be a sequence of deflecting units that guide the light to an eyepiece at the proximal end of the endoscope.

The distal optical assembly can comprise an entrance lens which is arranged in the direction of incident light before the entry surface of the first prism. The entrance lens can be arranged on the entry surface of the first input-side prism. This yields a compact optical arrangement.

Such object can also be achieved by a side-viewing endoscope with an optical system as described above.

Further features will become apparent from the description of embodiments together with the claims and the attached drawings. Embodiments can fulfill individual features or a combination of several features.

BRIEF DESCRIPTION OF THE DRAWINGS

The embodiments are described below, without restricting the general idea of the invention, based on exemplary embodiments in reference to the drawings, whereby we expressly refer to the drawings with regard to the disclosure of all details that are not explained in greater detail in the text. In the following.

In the drawings, the same or similar elements and/or parts are always provided with the same reference numbers; a reintroduction will therefore always be omitted.

DETAILED DESCRIPTION

Figure 2:
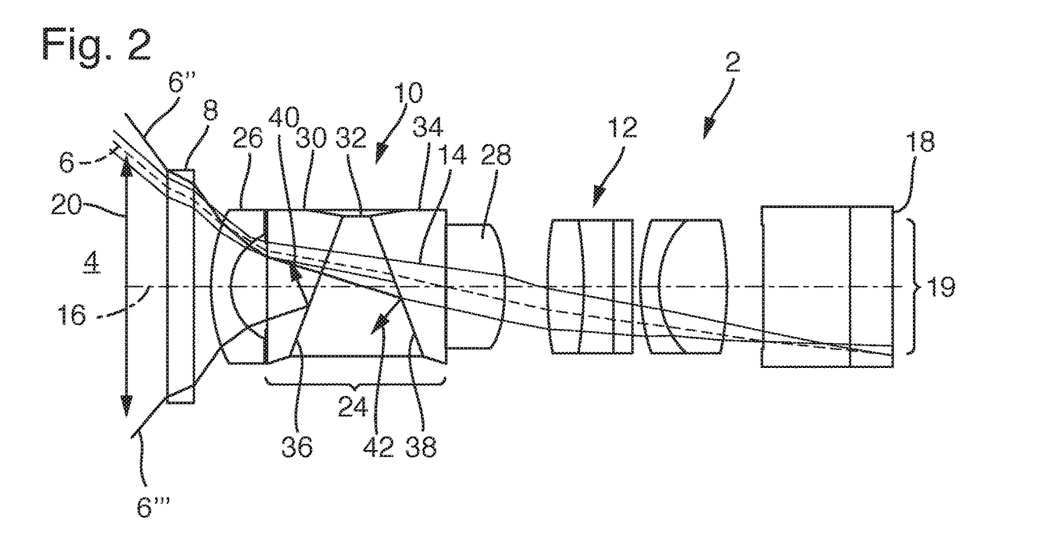
FIG. 2 illustrates an optical system in a schematically simplified longitudinal section.

FIG. 2 shows an optical system 2 with a direct view according to the German patent application DE 10 2016 214 025.6 by the applicant, also in a simplified and schematic longitudinal section view along a vertical sectional plane. The optical system 2 comprises a distal optical assembly 10 and a proximal optical assembly 12. The distal optical assembly 10 and the proximal optical assembly 12 define a beam path 14 in the optical system 2. Light bundles 6 (of which only one is shown as an example) from the object space 4 entering the optical system 2 from within the field of view 20 are mapped on a light-sensitive surface 19 of the image sensor 18.

The optical system 2 according to the depicted exemplary embodiment comprises a prism group 24 arranged in the beam path 14. The prism group 24 comprises at least one prism 30, 32, 34 and limits the field of view 20 of the optical system 2 on at least one side. Along with the prism group 24, the distal optical assembly 10 also comprises an entry lens 26 and an exit lens 28. The at least one prism 30, 32, 34 of the prism group 24 comprises a boundary surface 36, 38 on which the incident light beams 6" entering the optical system 2 from outside the field of view 20 are reflected out of the beam path 14 with total reflection.

The prism group 24 shown in FIG. 2 comprises, for example, a first prism 30, a second prism 32 and a third prism 34. The first prism 30 provides a first boundary surface 36 at which a first light bundle 40 (indicated by an arrow) is reflected out of the beam path 14. The second prism 32 provides a second boundary surface 38 at which a second light bundle 42 (also indicated by an arrow) is reflected out of the beam path 14 in another direction.

The light bundles reflected out of the beam path 14 enter the optical system 2 as light bundles 6" and 6'" from outside the field of view 20. In FIG. 2, the incident light bundle 6'" on the underside of the optical system 2 from outside the field of view 20 is completely reflected as a first light bundle 40 on the first boundary surface 36 and thus removed from the beam path 14. The incident light bundle 6" entering the upper side of the optical system 2 from outside the field of view 20 is completely reflected as a second light bundle 42 on the second boundary surface 38 and thus reflected out of the beam path 14.

The prism group 24 limits the field of view 20 on two mutually opposing sides, for example on a lower and an upper horizontal edge of the field of view 20. Incident light beams 6", 6'" entering the optical system 2, which enter from outside the field of view 20, are reflected out of the beam path 14 on these sides of the field of view 20. In the same way, by rotating the prism group 24 about the optical axis 16, a limitation, for example on the vertical edges of the field of view 20, can result as on the left or right side of the field of view 20. For this, the prism group 24 would have to be rotated by 90° about the optical axis 16; furthermore, it would have to be adapted to the required horizontal viewing angle (which is possibly larger than the vertical viewing angle). Such an adaptation takes place, for example, by a suitable choice of the inclination of the boundary surfaces 36, 38 with respect to the optical axis 16.

A further prism group not depicted in FIG. 2 can also be added. With such an exemplary embodiment, a first prism group 24 would be arranged like the prism group 24 shown in FIG. 2, and a second prism group would be arranged afterward in the direction of incident light, rotated by 90° about the optical axis 16. Thus, a limitation of the field of view 20 could be achieved on both the horizontal and vertical limits of the field of view 20.

Figure 3:
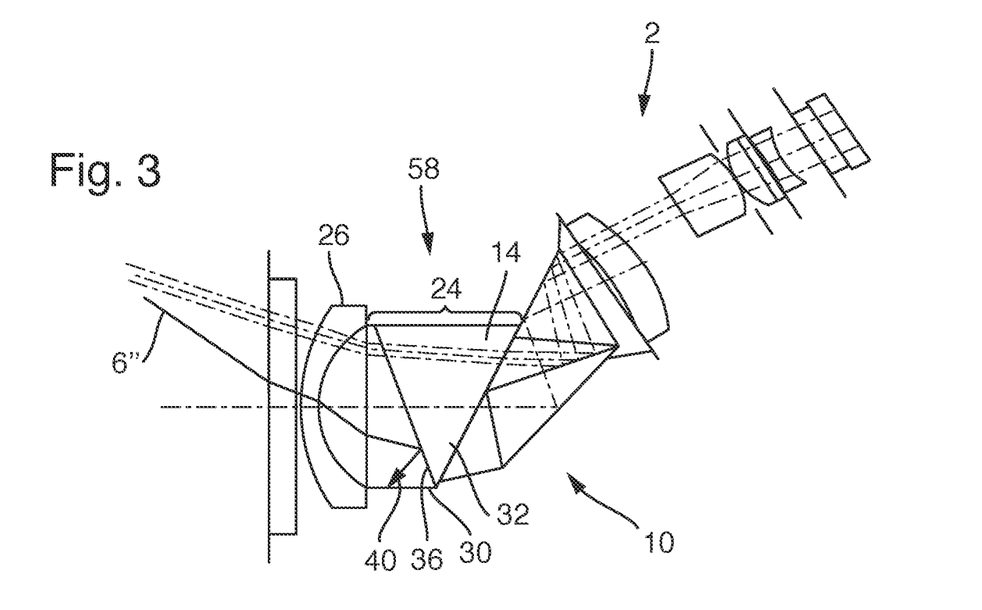
FIG. 3 illustrates an optical system of a stereo videoendoscope.

FIG. 3 shows another optical system 2 according to the German patent application DE 10 2016 214 025.6 by the applicant. The optical system 2 is, for example, the optical system 2 of a stereo video endoscope with a lateral view. The optical system 2 includes, as part of the deflecting prism group 58, a prism group 24, which includes a boundary surface 36 on which the incident light bundle 6" from outside the field of view 20 is reflected out of the beam path 14 as a first light bundle 40. The prism group 24 includes the first prism 30 and the second prism 32 for this purpose. Once again, a first air gap can be provided between the first boundary surface 36 of the first prism 30 so that total reflection takes place on the boundary surface 36. The first and second prisms 30, 32 can be configured in such a way that these replace the first deflecting prism 62 of the deflecting prism group 58; i.e. produce an equivalent optical effect (aside from the total reflection of light bundles 6" not coming from the field of view 20). The prism group 24, which in each case is a part of the distal optical assembly 10, removes undesirable scattered light directly at the beginning of the optical system 2. This increases the imaging quality of the optical system 2.

The prism group from FIG. 3 is structurally complex and large to build since it does not fit in a cylindrical envelope.

Figure 5:
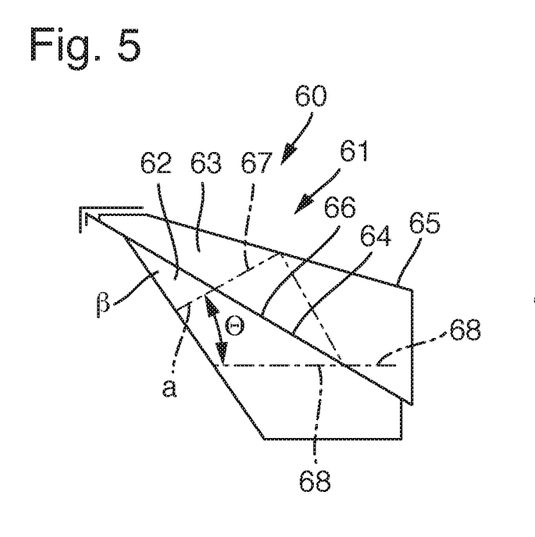
FIG. 5 illustrates an exemplary embodiment of a prism group with two prisms.

FIG. 5 shows a first exemplary embodiment of a prism group 61 of an optical system 60. This is a prism group 61 with two prisms, i.e., a first prism 62 and a second prism 63, that are separated from each other by a gap 64. Also shown in FIG. 5 are the path α of the central beam path 67 through the first prism 62, the wedge angle β of the first prism 62, as well as the lateral viewing angle θ. Starting at the entrance, the central beam path 67 runs through the first prism 62, the gap 64, the second prism 63, and undergoes a reflection at the first reflective surface 65, as well as another reflection at the second reflective surface 66 where the central beam path 67 enters the central longitudinal axis 68 of the endoscope. The passage through the gap 64 ensures that light beams which enter at a larger angle from further up in FIG. 5 are reflected away by total reflection and are omitted from the beam path.

Figure 6:
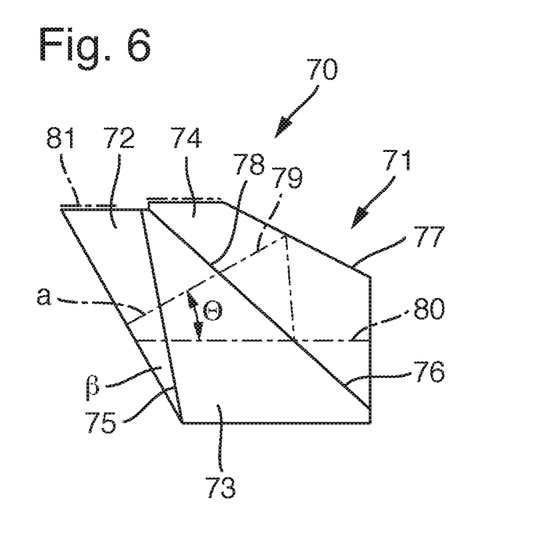
FIG. 6 illustrates an exemplary embodiment of a prism group with three prisms.

FIG. 6 shows a second exemplary embodiment of a prism group 71 of an optical system 70. This prism group 71 has three prisms 72, 73 and 74 which are separated from each other by two gaps 75, 76. Also discernible are the path α of the central beam path 79 through the first prism 72, the wedge angle β of the first prism 72, and the lateral viewing angle θ of the optical system 70 which is 30° in this exemplary embodiment. Just as in the previous example, the central beam path 79 is reflected twice at a first reflective surface 77 and a second reflective surface 78 from the lateral entry direction into the direction of the endoscope shaft parallel with the axis of symmetry. It is discernible that for example the first prism 72 has a top cut 81. The other prisms 73, 74 are also cut at their top sides, or respectively bottom sides. In comparison to the known prism system according to, for example, FIGS. 4a and 4b, it is notable that there is significantly less dead glass volume toward the bottom.

To a certain extent, FIG. 6 shows that the two gaps 75, 76 are arranged mirrored to each other relative to the first section of the central beam path 79 so that they cause a symmetrical expulsion by total reflection of light beams that enter from further up or further below outside of the visual field into the prism group 71.

Figure 7:
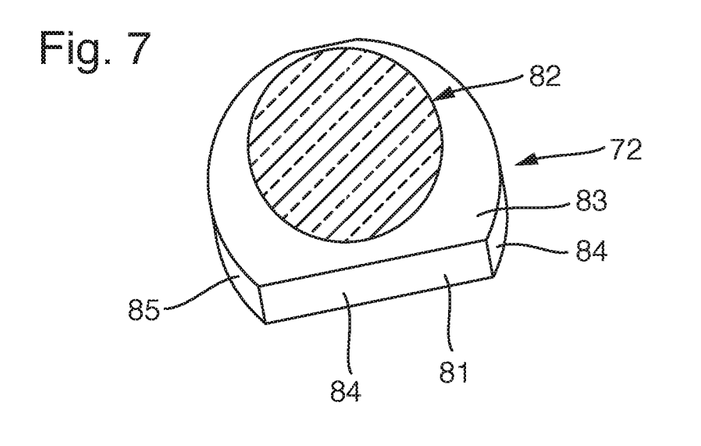
FIG. 7 illustrates a perspective view of the first prism of the prism group from FIG. 6, and FIGS. 8a and 8b illustrate details of an exemplary embodiment of a prism group with three prisms.

FIG. 7 shows a perspective view of the first prism 72 of the prism group 71 from FIG. 6 in which it is discernible that this prism 72 is fitted into a cylindrical envelope 85. The top cut 81 of the first prism 72 is also discernible as a transparent region 82 that is provided for the desired beam path as well as an opaquely coated edge 83 which can be coated with an anti-flare coating 84.

Figure 8A:
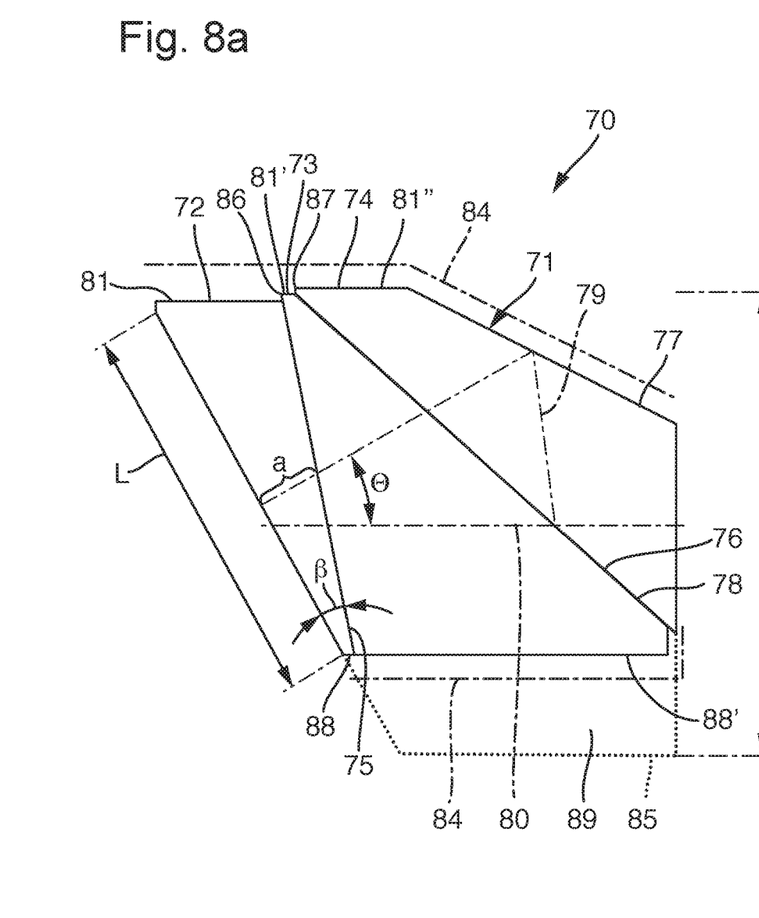
Figure 8B:
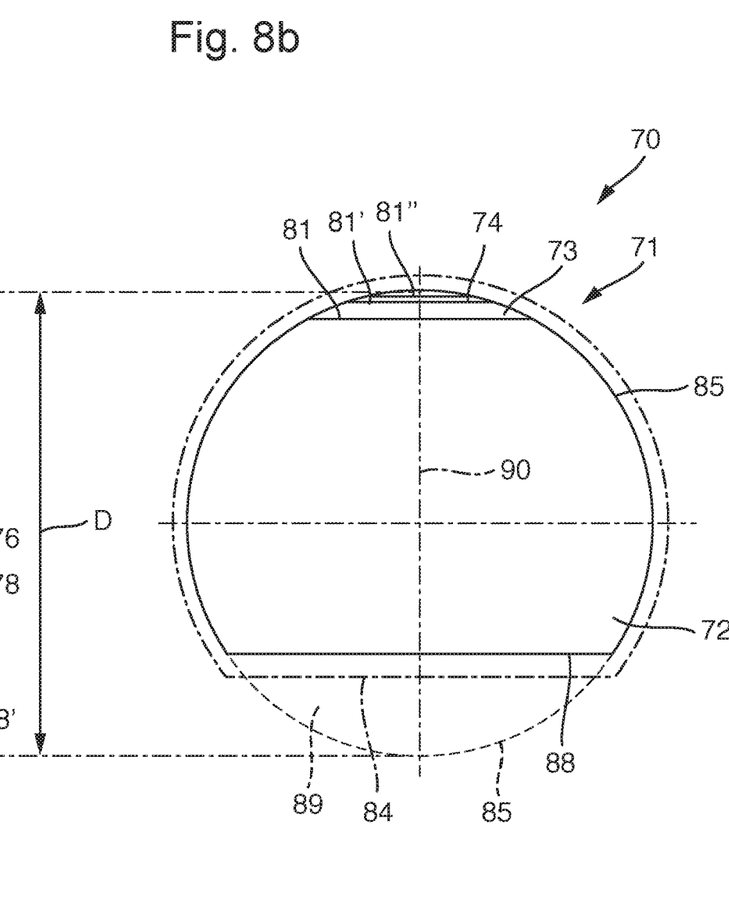

FIG. 8a shows a cross-sectional view of the embodiment according to FIG. 6 in greater detail. The plane of the cross-sectional view corresponds to the plane of symmetry 90 of the optical system 70 that is shown in FIG. 8b.

In addition to the angles $\beta$ and $\theta$ which are defined as above and the length $\alpha$ of the section of the central beam path 79 which runs through the first prism 72, the length L of the entry surface of the first prism 72 as well as the diameter D of the envelope 85 of the prism group 71 of the optical system 70 are shown in FIG. 8a. The length L of the entry surface of the first prism 72 is the length of the entry surface in the plane of symmetry 90 of the prism group in which the entire central beam path 79 also runs. The diameter D of the envelope is the same as the diameter of the circular projection of the envelope which is shown in FIG. 8b. FIG. 8b also shows the sequence of the upper cuts 81, 81', 81" of the three prisms 72, 73 and 74 which form a sequence of steps that are also discernible in FIG. 8a. These form stop edges 86, 87 on the top side of the prism group 71. FIGS. 8a and 8b also show the anti-flare coating 84 of the prism group 71 as well as the lower cuts 88, 88', 88" of the prisms 72, 73 and 74.

In FIG. 8a, it is also discernible that, after the second reflection, the central beam path 79 coincides with the central longitudinal axis 80 of the endoscope shaft. It is also discernible that the material of the prism group 71 in the bottom region does not completely fill the envelope 85; instead, a bottom empty space remains. In a completely assembled state, this is filled on the one hand by a corresponding holder which can also have space for light-conducting means such as light-conducting fibers.

The geometry of the prism 73 meets the conditions:

$\alpha < \cos\theta \cdot \tan\beta \cdot D/2$ as well as $L < D/\cos\theta$.

Given these conditions, it is reliably possible to find compact prism groups that can be fitted in a cylindrical envelope having minimal optical dead volume with a lateral view and simultaneously total reflection of laterally entering light beams at the gap or gaps of the prism group, and that accordingly require minimal installation space.

With the given lateral viewing angle $\theta$, it is for example accordingly possible to adjust the angle at which light beams entering from outside of the planned field of view can be removed by total reflection using the wedge angle $\beta$ of the first prism 72 and possibly the corresponding wedge angle of the second prism 73. The path length $\alpha$ can then be adjusted by shifting the first prism 72 at the boundary surface relative to the second prism 73. The diameter D can be specified corresponding to the available installation space, whereas the length L of the entrance surface of the first prism 72 then results from the combination of the selected parameters and the cuts to be selected relative to the cylindrical envelope.

While there has been shown and described what is considered to be preferred embodiments, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCE SIGNS

2 Optical system
4 Object space
6, 6', 6", 6''' Light bundles
8 Entry window
10 Distal optical assembly
12 Proximal optical assembly
14 Beam path
16 Optical axis
18 Image sensor
19 Light-sensitive surface
20 Field of view
22 Scattering center
24 Prism group
26 Entry lens
28 Exit lens
30 First prism
32 Second prism
34 Third prism
36 First boundary surface
38 Second boundary surface
40 First light bundle
42 Second light bundle
58 Deflecting prism group
60 Optical system
61 Prism group
62 First prism
63 Second prism
64 Gap
65 First reflective surface
66 Second reflective surface
67 Central beam path
68 Longitudinal axis of the endoscope shaft
70 Optical system
71 Prism group
72 First prism
73 Second prism
74 Third prism
75 First gap
76 Second gap
77 First reflective surface
78 Second reflective surface
79 Central beam path
80 Longitudinal axis of the endoscope shaft
81, 81', 81"Upper cut
82 Transparent region
83 Opaquely coated edge
84 Anti-flare coating
85 Cylindrical envelope
86, 87 Stop edge
88, 88', 88"Lower cut 89 Bottom empty space
90 Plane of symmetry
100 Distal optical assembly
102 First prism
104 Second prism
106 Gap
108 First reflective surface
110 Second reflective surface
112 Central beam path
114 Optically unused glass volume

What is claimed is:

1. An optical system for a side-viewing endoscope with a central beam path that has a distal lateral viewing angle θ relative to a longitudinal axis of an endoscope shaft of the endoscope, the optical system comprising:

a distal optical assembly having a prism group configured to deflect incident light from a field of view defined around the lateral viewing angle in a direction of the longitudinal axis of the endoscope shaft by means of reflection at a first reflective surface and at a second reflective surface;

wherein the prism group comprises two or more prisms, mutually adjacent boundary surfaces of the two or more prisms are arranged in pairs parallel to each other and are separated by a gap in each case, wherein a total reflection of incident light from outside a field of view takes place at a boundary surface between a prism of the two or more prisms and a corresponding gap, wherein the prism group, in a cross section taken perpendicular to the longitudinal axis, has a shape of a circular segment within a cylindrical envelope with a diameter D, and an input-side first prism of the prism group is configured to have a wedge-shape with a wedge angle β and an optical path length α of the central beam path;

an entry surface of the first prism has a length L, defined as a length of a line of intersection of the entry surface with a plane that is spanned by the central beam path; and the first prism meets the conditions:

$$\alpha < \cos\theta \cdot \tan\beta \cdot D/2 \text{ and } L < D/\cos\theta.$$

2. The optical system according to claim 1, wherein the prism group comprises the first prism, a second prism and a third prism, wherein the second prism is configured to have a wedge-shape, wherein a wedge angle of the second prism borders a side of the first prism opposite the wedge angle of the first prism, and the wedge angle of the first prism borders a side of the second prism opposite the wedge angle of the second prism so that the gaps between the first, second and third prisms are angled relative to the central beam path in different directions.

3. The optical system according to claim 2, wherein the wedge angle of the second prism is 2·β.

4. The optical system according to claim 1, wherein the gap is filled with a medium that has a lesser optical density than a glass used for the two or more prisms.

5. The optical system according to claim 4, wherein the medium is selected from a group consisting of a vacuum, an inert atmosphere or air.

6. The optical system according to claim 1, wherein the two or more prisms comprise at least the first prism and a second prism, at least one of the first prism and the second prism having one or more of a lower cut and an upper cut.

7. The optical system according to claim 6, wherein the lower cuts or upper cuts are formed stacked in height.

8. The optical system according to claim 1, further comprising a proximal optical assembly and at least one of an image sensor or an eyepiece disposed proximally to the proximal optical assembly.

9. The optical system according to claim 1, wherein the distal optical assembly comprises an entry lens arranged before the entry surface of the first prism in a direction of incident light.

10. A side-viewing endoscope comprising an optical system according to claim 1.

* * * * *